(12) United States Patent
Bourque

(10) Patent No.: US 11,814,528 B2
(45) Date of Patent: Nov. 14, 2023

(54) DIESTER OF BISPHENOL FLUORENE COMPOUNDS AND THERMOCHROMIC PIGMENT COMPOSITIONS COMPRISING THE SAME

(71) Applicant: Société BIC, Clichy (FR)

(72) Inventor: Alexander Bourque, Montevrain (FR)

(73) Assignee: Société BIC, Clichy (FR)

( * ) Notice: Subject to any disclaimer, the term of this patent is extended or adjusted under 35 U.S.C. 154(b) by 421 days.

(21) Appl. No.: 17/278,457

(22) PCT Filed: Sep. 20, 2019

(86) PCT No.: PCT/EP2019/075305
§ 371 (c)(1),
(2) Date: Mar. 22, 2021

(87) PCT Pub. No.: WO2020/064537
PCT Pub. Date: Apr. 2, 2020

(65) Prior Publication Data
US 2021/0363371 A1    Nov. 25, 2021

(30) Foreign Application Priority Data
Sep. 24, 2018  (EP) ..................................... 18306234

(51) Int. Cl.
*C09D 11/50* (2014.01)
*C09D 11/17* (2014.01)
(Continued)

(52) U.S. Cl.
CPC ................ *C09D 11/50* (2013.01); *B43K 7/00* (2013.01); *B43K 29/02* (2013.01); *C07C 69/28* (2013.01);
(Continued)

(58) Field of Classification Search
CPC .......... C09D 11/50; C09D 11/17; B43K 7/00; B43K 29/02; C07C 69/28; C07C 2603/18;
(Continued)

(56) References Cited

U.S. PATENT DOCUMENTS 5,149,886 A    9/1992  Orth et al.
8,865,621 B2 * 10/2014  Kwan ................... C09D 11/50
                                                503/201
(Continued)

FOREIGN PATENT DOCUMENTS

EP    0529812    3/1993
EP    0396418    7/1997
(Continued)

OTHER PUBLICATIONS

Extended European Search Report dated Mar. 11, 2019 in priority patent application No. 18306234.8, 6 pgs.
(Continued)

*Primary Examiner* — David J Walczak
(74) *Attorney, Agent, or Firm* — Ruggiero, McAllister & McMahon LLC

(57) ABSTRACT

There is a compound represented by the following formula (I):

(Continued)

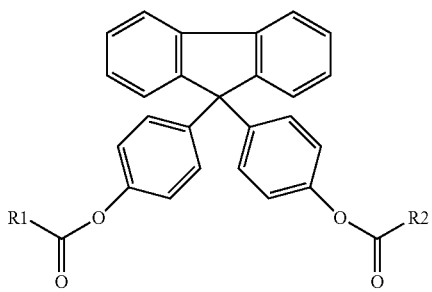

in which R1 and R2, identical or different, represent a $C_2$-$C_{30}$ alkyl group, a $C_2$-$C_{30}$ alkenyl group, a $C_2$-$C_{30}$ alkynyl group, or a $C_2$-$C_{30}$ alkoxy group, the alkyl, alkenyl, alkynyl, or alkoxy groups being optionally substituted with at least one hydroxy, halogen, amino, $C_1$-$C_8$ alkyl, or $C_1$-$C_8$ alkoxy group, as a temperature change regulating agent in a thermochromic ink composition. There also are thermochromic pigment microcapsules having a compound of formula (I) according to the disclosure, to ink compositions having such thermochromic pigment microcapsules, and to writing instruments comprising such ink compositions.

20 Claims, 1 Drawing Sheet

(51) Int. Cl.
| | |
|---|---|
| *B43K 7/00* | (2006.01) |
| *B43K 29/02* | (2006.01) |
| *C07C 69/28* | (2006.01) |
| *C09B 57/00* | (2006.01) |
| *C09B 67/22* | (2006.01) |
| *C09K 9/02* | (2006.01) |
| *C09B 5/00* | (2006.01) |

(52) U.S. Cl.
CPC ............ *C09B 5/00* (2013.01); *C09B 67/0033* (2013.01); *C09D 11/17* (2013.01); *C09K 9/02* (2013.01); *C07C 2603/18* (2017.05); *C09K 2211/1007* (2013.01); *C09K 2211/1011* (2013.01)

(58) Field of Classification Search
CPC ....... C09B 57/00; C09B 67/0033; C09K 9/02; C09K 2211/1007; C09K 2211/1011
USPC ......... 503/200–226; 106/31.32, 31.64, 31.23
See application file for complete search history.

(56) References Cited

U.S. PATENT DOCUMENTS

| | | | |
|---|---|---|---|
| 10,358,570 B2 | 7/2019 | Ono | |
| 2023/0167325 A1* | 6/2023 | Bourque | C09D 11/50 401/209 |

FOREIGN PATENT DOCUMENTS

| | | |
|---|---|---|
| EP | 3009493 | 4/2016 |
| EP | 3333240 | 6/2018 |
| JP | 8-175028 | 7/1996 |
| JP | 2008-150483 | 7/2008 |
| WO | 2017-022471 | 2/2017 |

OTHER PUBLICATIONS

T.M. Fruze et al, "Preparation of the dimethacrylate of 9,9-di-(4-hydroxyphenyl)fluorene—A new compound in a series of dimethacrylates of bisphenols", Division of chemical Russ Chem Bull 19, 185 (1970). https://doi.org/10.1007/BF00913957, 1 page.
International Search Report dated Nov. 26, 2019 in corresponding PCT International Patent Application No. PCT/EP2019/075305, 5 pgs.
Written Opinion dated Nov. 26, 2019 in corresponding PCT International Patent Application No. PCT/EP2019/075305, 6 pgs.

* cited by examiner

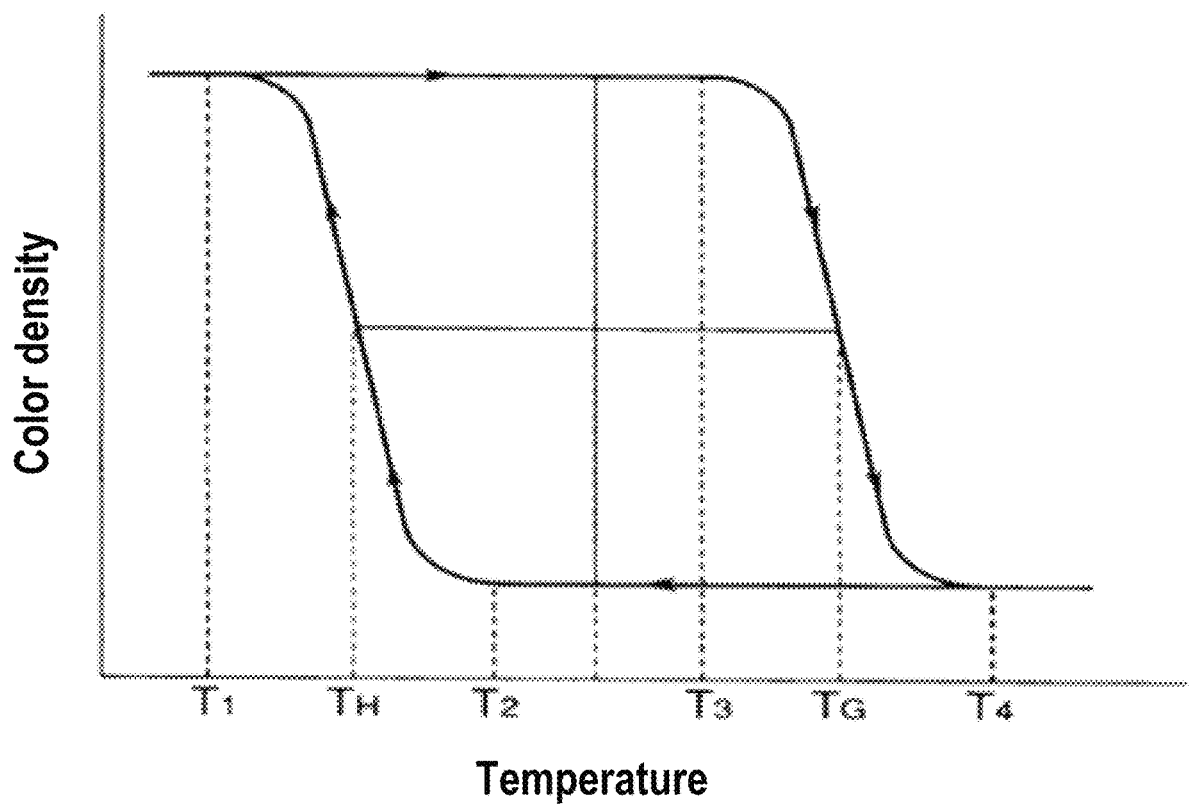

DIESTER OF BISPHENOL FLUORENE COMPOUNDS AND THERMOCHROMIC PIGMENT COMPOSITIONS COMPRISING THE SAME

CROSS REFERENCE TO RELATED APPLICATION(S)

This application claims priority from PCT Application N° PCT/EP2019/075305, filed on Sep. 20, 2019, now published as WO2020/064537, which claims priority based on European Patent Application No. 18306234.8, filed on Sep. 24, 2018, the entire contents of both of which are incorporated herein by reference.

FIELD OF THE DISCLOSURE

The present disclosure relates to diester of bisphenol fluorene compounds and their use as a reaction medium in thermochromic pigment compositions. The present disclosure also concerns thermochromic pigment microcapsules comprising such thermochromic pigment compositions, thermochromic ink compositions comprising such thermochromic pigment microcapsules, and finally writing instruments comprising such thermochromic ink compositions.

DESCRIPTION OF THE RELATED ART

JP2008150483 discloses a thermochromic color-change composition comprising a bisphenol fluorene compound as an electron-accepting compound (B). However, when used as a reaction medium (C) in thermochromic pigment composition, the bisphenol fluorene compound of JP2008150483 provides no thermochromic effect.

SUMMARY OF THE DISCLOSURE

Thermochromic pigment compositions exhibit reversible discoloration properties related to a change in temperature. They display reversible color-change between colored and decolored states with prominent hysteresis characteristics due to temperature change, and retain either a colored state or a decolored state in an interchangeable and reversible manner even after terminating the application of heat or cold required for the color-change. These compositions find application when ink marking requires repeated erasures.

The thermochromic effect of an ink works through the combination of the following three compounds:
(A) an electron-donating color-developing organic compound (leuco-dye compound),
(B) an electron-accepting compound (color developer compound), and
(C) a compound serving as a reaction medium which controls color reaction between the components (A) and (B), and capable of leading to a reversible electron-donating/accepting reaction attributable to compounds (A) and (B).

Temperature changes reversibly cause coloring or discoloration of the inks. For the thermochromic ink compositions of the present disclosure, the increases in temperature will cause erasure of the ink, while cooling the ink will cause the color to reappear. These changes follow the scheme of FIG. 1. In this scheme, the decoloration onset temperature of the ink color is T3, the complete discoloration temperature is T4 and TG is the average temperature between T3 and T4. Conversely, the temperature at which the color of the ink begins to reappear is T2, the complete recoloration temperature is T1 and TH is the average temperature between T1 and T2. The color-change hysteresis width (ΔH) is the difference between (TH) and (TG).

Surprisingly, the inventors have discovered novel diester of bisphenol fluorene compounds allowing the preparation of thermochromic pigment microcapsules having optimal melting and crystallization temperature ranges, which correspond respectively to the discoloration and recoloration temperatures. The compounds of the disclosure thus show many advantages to be used as regulating agents of temperature change in thermochromic pigment compositions: they exhibit outstanding hysteresis characteristics and an extremely high color contrast between the colored state and the discolored state. The thermochromic ink compositions comprising the diester of bisphenol fluorine compounds of the disclosure also offer the advantage of totally disappearing at a temperature close to 70° C., and therefore have the advantage of being used in hot countries. In addition, the thermochromic pigment composition of the disclosure has UV resistance properties, these properties being intrinsic to the compound of the disclosure, without the need to add anti-UV agents in the composition.

BRIEF DESCRIPTION OF THE DRAWING

FIG. 1 is a plot depicting the coloration or discoloration of the thermochromic ink compositions of the present disclosure as a function of temperature.

DETAILED DESCRIPTION OF THE DISCLOSURE

The present disclosure thus relates to the use of a diester of bisphenol fluorene compound represented by the following formula (I) as a temperature change regulating agent in a thermochromic ink composition:

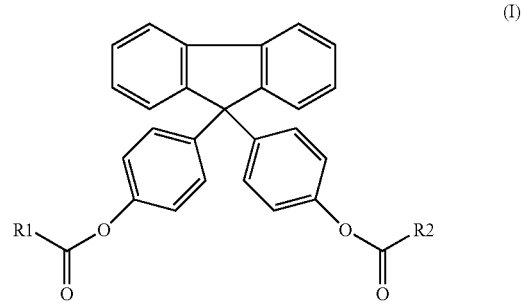

wherein R1 and R2, identical or different, represent a $C_2$-$C_{30}$ alkyl group, a $C_2$-$C_{30}$ alkenyl group, a $C_2$-$C_{30}$ alkynyl group, or a $C_2$-$C_{30}$ alkoxy group, the alkyl, alkenyl, alkynyl, or alkoxy groups being optionally substituted with at least one hydroxy, halogen, amino, $C_1$-$C_8$ alkyl, or $C_1$-$C_8$ alkoxy group.

Such a temperature change regulating agent is capable of leading to a reversible electron-donating/accepting reaction between an electron-donating color-developing organic compound (A) and an electron-accepting compound (B).

According to a preferred embodiment, R1 and R2 are identical and represent a linear or branched $C_2$-$C_{30}$ alkyl group, more specifically a linear or branched $C_4$-$C_{20}$ alkyl group, and even more specifically a linear or branched $C_6$-$C_{18}$ alkyl group.

According a preferred embodiment, R1 and R2 are identical and represent a linear or branched $C_6$-$C_{30}$ alkyl group, more specifically a linear or branched $C_6$-$C_{18}$ alkyl group, and even more specifically a linear $C_{13}$ alkyl group.

Another subject-matter of the disclosure is a diester of bisphenol fluorine compound represented by the following formula (II):

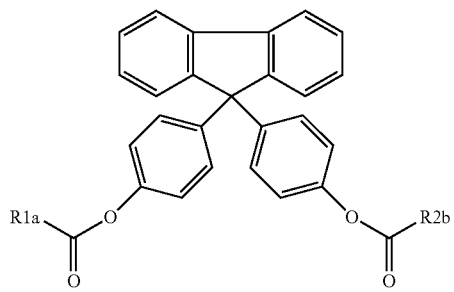

(II)

wherein R1a and R2b, identical or different, represent a linear or branched $C_6$-$C_{30}$ alkyl group, more specifically a linear or branched $C_6$-$C_{18}$ alkyl group, and even more specifically a linear $C_{13}$ alkyl group.

The compound represented by the formula (I) according to the disclosure may be prepared according to a first method comprising the step of reacting bisphenol fluorene with acid chlorides of formula R1C(O)Cl and R2C(O)Cl, wherein R1 and R2 are identical or different, and represent a $C_2$-$C_{30}$ alkyl group, a $C_2$-$C_{30}$ alkenyl group, a $C_2$-$C_{30}$ alkynyl group, or a $C_2$-$C_{30}$ alkoxy group, the alkyl, alkenyl, alkynyl, or alkoxy groups being optionally substituted with at least one hydroxy, halogen, amino, $C_1$-$C_8$ alkyl, or $C_1$-$C_8$ alkoxy group, according to the following reaction scheme:

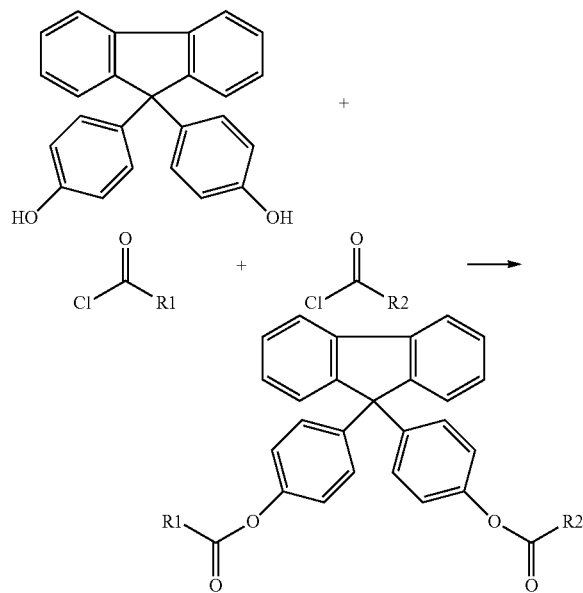

In this first method, the molar ratio bisphenol fluorene/acid chloride R1C(O)Cl/acid chloride R2C(O)Cl is more specifically of 1/1/1.

In this first method, the reaction is more specifically carried out at a temperature ranging from −30 to 20° C., even more specifically from −10 to 10° C.

The compound represented by the formula (I) according to the disclosure may also be prepared according to a second method comprising the step of reacting bisphenol fluorene with a carboxylic acid of formula R1COOH, wherein R1 represents a $C_2$-$C_{30}$ alkyl group, a $C_2$-$C_{30}$ alkenyl group, a $C_2$-$C_{30}$ alkynyl group, or a $C_2$-$C_{30}$ alkoxy group, the alkyl, alkenyl, alkynyl, or alkoxy groups being optionally substituted with at least one hydroxy, halogen, amino, $C_1$-$C_8$ alkyl, or $C_1$-$C_8$ alkoxy group, according to the following reaction scheme:

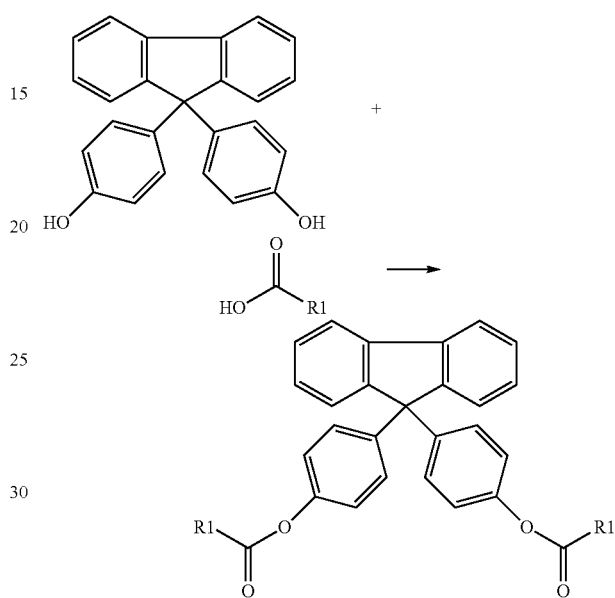

In this second method, the molar ratio bisphenol fluorene/carboxylic acid R1COOH ranges more specifically from ½ to ⅙, and more specifically is of ¼.

In this second method, the reaction is more specifically carried out at a temperature ranging from 120 to 200° C., even more specifically from 140 to 160° C.

Another subject-matter of the disclosure is a thermochromic pigment composition comprising:
(A) an electron-donating color-developing organic compound (leuco-dye compound),
(B) an electron-accepting compound (color developer compound), and
(C) a compound of formula (I) according to the disclosure as a reaction medium which controls color reaction between the components (A) and (B).

It is quite surprising that the inventors have discovered that diester of bisphenol fluorene compounds according to the disclosure have particular melting and crystallization temperatures that allow their use as a compound (C) or a temperature change regulating agent in thermochromic pigment compositions.

Thus, the disclosure also describes use of a diester of bisphenol fluorene compound of formula (I) as a temperature change regulating agent in a thermochromic ink composition. Such a temperature change regulating agent is capable of leading to a reversible electron-donating/accepting reaction between an electron-donating color-developing organic compound (A) and an electron-accepting compound (B).

The weight ratios of the compounds (A), (B) and (C) are influenced by the structure and reactivity of each of these compounds.

The amount by weight of electron-donating color-developing organic compound (A) may vary from 1 to 10%, more specifically from 1 to 6%, and even more specifically from 2 to 4%, by weight relative to the total weight of the thermochromic pigment composition.

The amount by weight of electron-accepting compound (B) may vary from 1 to 20%, more specifically from 1 to 14%, and even more specifically from 4 to 10%, by weight relative to the total weight of the thermochromic pigment composition.

The amount by weight of compound (C) of formula (I) acting as a reaction medium may vary from 70 to 98%, more specifically from 80 to 98%, and even more specifically from 86 to 94% by weight relative to the total weight of the thermochromic pigment composition.

Thus, the thermochromic pigment composition of the disclosure may comprise:
- (A) from 1 to 10%, more specifically from 1 to 6%, and even more specifically from 2 to 4%, by weight of at least one electron-donating color-developing organic compound,
- (B) from 1 to 20%, more specifically from 1 to 14%, and even more specifically from 4 to 10%, by weight of at least one electron-accepting compound, and
- (C) from 70 to 98%, more specifically from 80 to 98%, and even more specifically from 86 to 94%, by weight of at least one compound of formula (I).

More specifically, the thermochromic pigment composition of the disclosure has a color-change hysteresis width (ΔH) after encapsulation ranging from 20 to 80° C., more specifically from 30 to 80° C., and even more specifically from 40 to 70° C.

As the organic dye-electron donor compound (A), conventionally known compounds such as diphenylmethane phthalides, phenylindolyl phthalides, indolylphthalides, diphenylmethane azaphthalides, phenylindolyl azaphthalides, fluoranes, styrylquinolines and lactones diazarhodamine may be mentioned without limitation, examples of these compounds being presented hereinafter.

The organic dye-electron donor compound (A) can thus be chosen from
- 3-(4-diethylamino-2-ethoxyphenyl)-3-(1-ethyl-2-methyl indol-3-yl)-4-azaphthalide (Blue 63, CAS number: 69898-40-4),
- 3,3-bis(p-dimethylaminophenyl)-6-dimethylaminophthalate (CAS number: 1552-42-7),
- 2'-chloro-6'-(diethylamino)-3'-methylfluorane (CAS number: 21121-62-0),
- 6'-(diethylamino)-1',3'-dimethylfluorane (CAS number: 21934-68-9),
- 6'-(diethylamino)-1',3'-dimethylfluorane (CAS number: 21934-68-9),
- 2-chloro-6-(diethylamino)-fluorane (CAS number: 26567-23-7),
- 3-diethylaminobenzofluorane (CAS number: 26628-47-7),
- 3',6'-bis(diethylamino)-2-(4-nitrophenyl)spiro[isoindole-1,9'-xanthene]-3-one (CAS number: 29199-09-5),
- 2-phenylamino-3-methyl-6-diethylaminofluorane (CAS number: 29512-49-0),
- 2'-(dibenzylamino)-6'-(diethylamino)fluoran (CAS number: 34372-72-0),
- 2-(2,4-dimethylphenylamino)-3-methyl-6-diethylaminofluorane (Black 15, CAS number: 36431-22-8),
- 3-(1,2-dimethyl-3-indolyl)-3-[4-(diethylamino)-2-methylphenyl]phthalide (CAS number: 36499-49-7),
- 3',6'-dimethoxyfluorane (CAS number: 36886-76-7),
- 3,3-bis-(1-butyl-2-methyl-indol-3-yl)-3H-isobenzofuran-1-one (Red 40, CAS number: 50292-91-6),
- 3,3-bis-(2-methyl-1-octyl-1H-indol-3-yl)-3H-isobenzofuran-1-one (CAS number: 50292-95-0),
- 2'-anilino-6'-[ethyl(p-tolyl)amino]-3'-methylspiro[isobenzofuran-1(3H),9'-[9H]xanthene]-3-one (CAS number: 59129-79-2),
- 3-(4-diethylamino-2-ethoxyphenyl)-3-(1-ethyl-2-methyl-indol-3-yl)-4-azaphthalide (CAS number: 69898-40-0),
- 3-(N-ethyl-n-isopentylamino)-6-methyl-7-anilino-fluorene (CAS number: 70516-41-5),
- 3-[4-(diethylamino)phenyl]-3-(1-ethyl-2-methyl-1H-indol-3-yl)phthalide (CAS number: 75805-17-3),
- 2'-(2-chloroanilino)-6'-(dibutylamino) fluoran (CAS number: 82137-81-3),
- 2-phenylamino-3-methyl-6-dibutylaminofluorane (CAS number: 89331-94-2),
- 3-(1-butyl-2-methyl-1H-indol-3-yl)-6-(dimethylamino)-3-[4-(dimethylamino)phenyl]-3-(1(3H)-isobenzofuranone (CAS number: 92453-31-1),
- 7-(4-diethylamino-2-hexyloxyphenyl)-7-(1-ethyl-2-methyl-1H-indol-3-yl)-7H-furo[3, 4-b]pyridin-5-one (Blue 203, CAS number: 98660-18-5),
- 7,7-bis[4-(diethylamino)-2-ethoxyphenyl]furo[3,4-b]pyridin-5-one (CAS number: 132467-74-4),
- N,N-dimethyl-4-[2-[2-(octyloxy)phenyl]-6-phenyl-4-pyridinyl]benzenamine (Yellow CK37, CAS number: 144190-25-0),
- 3-(2,2-bis(1-ethyl-2-methylindol-3-yl)vinyl)-3-(4-diethylaminophenyl)-phthalide (CAS number: 148716-90-9),
- and mixtures thereof.

According to a preferred embodiment, the organic dye-electron donor compound (A) is selected from
- 3-(4-diethylamino-2-ethoxyphenyl)-3-(1-ethyl-2-methyl-indol-3-yl)-4-azaphthalide (Blue 63, CAS number: 69898-40-4),
- 2'-(dibenzylamino)-6'-(diethylamino)fluoran (CAS number: 34372-72-0),
- N, N-dimethyl-4-[2-[2-(octyloxy)phenyl]-6-phenyl-4-pyridinyl]benzenamine (Yellow CK37, CAS number: 144190-25-0),
- 7-(4-diethylamino-2-hexyloxyphenyl)-7-(1-ethyl-2-methyl-1H-indol-3-yl)-7H-furo[3,4-b]pyridin-5-one (Blue 203, CAS number: 98660-18-5),
- 2-(2,4-dimethylphenylamino)-3-methyl-6-diethylaminofluoran (Black 15, CAS number: 36431-22-8),
- 3,3-bis-(1-butyl-2-methyl-indol-3-yl)-3H-isobenzofuran-1-one (Red 40, CAS number: 50292-91-6),
- and mixtures thereof.

As the electron-accepting compound (B), mention may be made, without limitation, of compounds having an active proton, such as compounds having a phenolic hydroxyl group (monophenols or polyphenols) such as bisphenols or trisphenols, and derivatives thereof which have substituents such as alkyl, aryl, acyl, alkoxycarbonyl, carboxy and esters thereof, and amido groups, halogen atoms, and phenol-aldehyde condensation resins.

In the electron-accepting compounds (B) of the disclosure, the following terms mean:

Alkyl: a saturated, linear or branched, $C_1$-$C_{20}$, more specifically $C_1$-$C_{12}$, more specifically $C_1$-$C_6$, and even more specifically $C_1$-$C_4$, hydrocarbon-based aliphatic group. The term "branched" means that at least one lower alkyl group such as methyl or ethyl is carried by a linear alkyl chain. As the alkyl group, there may be mentioned, for example, methyl, ethyl, n-propyl, i-propyl, n-butyl, t-butyl and n-pentyl.

Aryl: any functional group or substituent derived from at least one aromatic ring; an aromatic ring corresponds to any planar mono- or polycyclic group comprising a delocalized π-system in which each atom of the cycle comprises a p-orbital, the p-orbital overlapping each other; among such aryl groups there may be mentioned phenyl, biphenyl, naphthalene and anthracene groups. The aryl groups of the disclosure more specifically comprise from 4 to 12 carbon atoms, and even more specifically from 5 to 6 carbon atoms. Even more specifically, the aryl group of the disclosure is a phenyl group.

Thus, the electron-accepting compound (B) may be chosen from
2,2-bis (4-hydroxy-3-methylphenyl)propane (bisphenol C, CAS number: 79-97-0),
4-hexyl-1,3-dihydroxybenzene (4-hexylresorcinol, CAS number: 136-77-6),
4,4'-cyclohexylidenebisphenol (BPZ, CAS number: 843-55-0),
4,4'-(hexafluoroisopropylidene)diphenol (bisphenol AF, CAS number: 1478-61-1),
4,4'-(1-phenylethylidene)bisphenol (CAS number: 1571-75-1),
2,2'-dihydroxybiphenyl (CAS number: 1806-29-7),
4,4'-ethylidenebisphenol (CAS number: 2081-08-5),
4,4'-(1,4-phenylenediisopropylidene)bisphenol (CAS number: 2167-51-3),
1,1-bis(4-hydroxy-3-methylphenyl)cyclohexane (CAS number: 2362-14-3),
9,9-bis (4-hydroxyphenyl)fluorene (CAS number: 3236-71-3),
4,4'-(1,3-phenylenediisopropylidene)bisphenol (CAS number: 13595-25-0),
1,1,1-tris(4-hydroxyphenyl)ethane (CAS number: 27955-94-8),
4,4'-(2-ethylhexylidene)diphenol (CAS number: 74462-02-5),
α,α,α'-tris(4-hydroxyphenyl)-1-ethyl-4-isopropylbenzene (CAS number: 110726-28-8),
4-(1,1,3,3-tetramethylbutyl)phenol (CAS number: 140-66-9),
4-hydroxydiphenyl ether (CAS number: 831-82-3),
bis(2-hydroxy-1-naphthyl)methane (CAS number: 1096-84-0),
4-(methylsulfonyl)phenol (CAS number: 14763-60-1),
4-hydroxyphenyl-4'-isopropoxyphenyl sulfone (CAS number: 95235-30-6),
4,4'-dihydroxybiphenyl (CAS number: 92-88-6),
4-hydroxybiphenyl (CAS number: 92-69-3),
p-hydroxycumene (CAS number: 99-89-8),
2,4-dihydroxybenzophenone (CAS number: 131-56-6),
hydroquinone monomethyl ether (HQMME, CAS number: 150-76-5),
3-n-pentadecylphenol (CAS number: 501-24-6),
4-(2-phenyl isopropyl)phenol (CAS number: 599-64-4),
5-chloro-2-(2,4-dichlorophenoxy)phenol (CAS number: 3380-34-5),
N-(p-toluenesulfonyl)-N'-(3-(p-toluenesulfonyloxy)phenyl)urea (CAS number: 232938-43-1),
2,2-bis (3,5-dibromo-4-hydroxyphenyl)propane (CAS number: 79-94-7),
4,4'-isopropylidenediphenol (CAS number: 80-05-7),
and the 4,4'-sulfonyldiphenol (BPS, CAS number: 80-09-1).

According to a preferred embodiment, the electron-accepting compound (B) is selected from
2,2-bis(4-hydroxy-3-methylphenyl)propane (bisphenol C, CAS number: 79-97-0),
4-hexyl-1,3-dihydroxybenzene (4-hexylresorcinol, CAS number: 136-77-6),
4,4'-cyclohexylidenebisphenol (BPZ, CAS number: 843-55-0),
4,4'-(hexafluoroisopropylidene)diphenol (bisphenol AF, CAS number: 1478-61-1),
4,4'-(1-phenylethylidene)bisphenol (CAS number: 1571-75-1),
2,2'-dihydroxybiphenyl (CAS number: 1806-29-7),
4,4'-(1,4-phenylenediisopropylidene)bisphenol (CAS number: 2167-51-3),
1,1-bis(4-hydroxy-3-methylphenyl)cyclohexane (CAS number: 2362-14-3),
9,9-bis(4-hydroxyphenyl)fluorene (CAS number: 3236-71-3),
4,4'-(1,3-phenylenediisopropylidene)bisphenol (CAS number: 13595-25-0),
1,1,1-tris(4-hydroxyphenyl)ethane (CAS number: 27955-94-8),
4,4'-(2-ethylhexylidene)diphenol (CAS number: 74462-02-5),
α,α,α'-tris(4-hydroxyphenyl)-1-ethyl-4-isopropylbenzene (CAS number: 110726-28-8),
and mixtures thereof.

The thermochromic pigment composition of the disclosure is prepared by dissolving the compounds (A) and (B) in the diester of bisphenol fluorene compound of formula (I) as defined according to the disclosure, and then stirring until a homogeneous mixture is obtained using a stirrer such as a homo-mixer or a disperser.

The compounds (A) and (B) thus associated with the diester of bisphenol fluorene compound of formula (I) of the disclosure can be formulated in the form of microcapsules. Thus, the thermochromic pigment composition of the disclosure is encapsulated in microcapsules to form microencapsulated thermochromic pigments. Such thermochromic pigment microcapsules constitute another subject-matter of the disclosure. They have advantageous characteristics insofar as they are resistant to mechanical stresses, insoluble and therefore dispersible in water, and slow agglomeration. The melting temperature (or discoloration temperature T4) of the thermochromic pigment composition within the microcapsules of the disclosure may vary from 20 to 80° C., more specifically from 30 to 80° C., and even more specifically from 40 to 70° C.

The crystallization temperature (or recoloration temperature T1) of the thermochromic pigment composition within the microcapsules of the disclosure may vary from −40 to 20° C., more specifically from −30 to 10° C., and even more specifically from −20 to 0° C.

The microcapsules comprising the thermochromic pigment composition of the disclosure has a mean diameter ranging from 0.5 to 30 μm, more specifically from 1 to 10 μm, and even more specifically from 3 to 5 μm. This average diameter corresponds to the volume d90 and means that 90% by volume of the microcapsules are smaller than the indicated value of d90. This average diameter can be determined by laser granulometry using a Zetasizer Nano ZS system from Malvern.

The microencapsulation methods used include, without limitation, conventional methods, such as:
chemical processes which rely on the in situ formation of the microcapsule shell. Representative examples of chemical methods include complex coacervation, interfacial polymerization (IFP), polymer-polymer incompatibility, in-situ polymerization, centrifugal force process, and submerged nozzle process, the interfacial polymerization (IFP) being the preferred one, physico-chemical processes, for example by phase separation or coacervation, by evaporation-extraction of solvent, by thermal gelation of emulsions (hot melt), or mechanical processes, for example by nebulization/drying (spray drying), by gelling or freezing drops, by coating in a fluidized bed (spray-coating).

The microcapsules comprising the thermochromic pigment composition of the disclosure are more specifically based on aminoplast resin, and more specifically based on melamine resin, urea resin or benzoguanamine resin.

The microcapsules comprising the thermochromic pigment composition of the disclosure are more specifically prepared by in situ polymerization from melamine resin.

Another object of the disclosure is a thermochromic ink composition comprising thermochromic pigment microcapsules according to the disclosure, and a carrier.

For the purposes of the present disclosure, the term "thermochromic ink composition" means an ink which is intended to be used in a writing instrument such as ballpoint pens, brush pens, colored pencils, markers, highlighters, chalks and felt pens; it should not be confused with a printing ink used in printing machines and which does not correspond to the same technical constraints, and thus to the same specifications. Indeed, a "thermochromic ink composition" intended to be used in a writing instrument within the framework of the disclosure must not contain solid particles of which the size is greater than the channels of the writing instrument, in order to avoid blocking them, which would inevitably lead to writing being irreversibly stopped. In addition, it must not be too fluid, so as to avoid leaks during writing. However, it must be sufficiently fluid to facilitate the flow of the writing action. In addition, it must allow an ink flow rate suitable for the writing instrument used, in particular a flow rate of between 10 and 700 mg/200 m of writing, more specifically between 250 and 650 mg/200 m of writing. It must also dry sufficiently rapidly to avoid smudging of the writing medium. It must also avoid the problems of ink migration (bleeding) over time. Thus, the thermochromic ink composition of the disclosure will be suitable for the writing instrument for which it is intended.

The thermochromic pigment microcapsules of the disclosure present in the ink composition represent from 5 to 40%, more specifically 15 to 30%, and even more specifically 15 to 25%, by weight relative to the total weight of the thermochromic ink composition.

The thermochromic ink composition of the disclosure is also mainly composed of water. More specifically, the water represents 40 to 80% by weight of the total weight of the thermochromic ink composition.

It may further comprise one or more solvents miscible with water. Thus, the thermochromic ink composition of the disclosure may contain an organic or aqueous solvent, more specifically an aqueous solvent.

Among the solvents that can be added to the thermochromic ink composition, mention may be made of polar solvents miscible in water such as:

alcohols: linear or branched alcohols in $C_1$-$C_{15}$ such as isopropanol, butanol, isobutanol, pentanol, benzyl alcohol, glycerin, diglycerin, polyglycerin, esters such as ethyl acetate or propyl acetate, carbonate esters such as propylene carbonate or ethylene carbonate, ketones such as methylisobutylketone (MIBK), acetone or cyclohexanone, glycols such as ethylene glycol, diethylene glycol, triethylene glycol, propylene glycol, polyethylene glycol, ethylene glycol monomethyl ether (EGME), 3-butylene glycol and thioethylene glycol, amides such as dimethylacetamide or dimethylformamide, and their mixtures.

The solvent or solvents may represent from 5 to 20% by weight of the total weight of the thermochromic ink composition.

The thermochromic pigment microcapsules of the disclosure may also be mixed with one or more specific adjuvants which may play different roles depending on the intended end use. These applications may include inks for writing tools such as ballpoint pens, brush pens, colored pencils, markers, highlighters, chalks and felt pens. The thermochromic pigment microcapsules of the disclosure may also be added to a thermoplastic or thermosetting resin composition to form moldings.

Among the adjuvants mentioned above, mention may be made of:

rheology modifiers (rheofluidifying agent) capable of generating a gelling effect, such as xanthan gum or gum arabic, defoamers, such as aqueous dispersions of modified polysiloxane (MOUSSEX® from Synthron), pH regulators, such as sodium hydroxide, triethanolamine, surfactants, such as polyether polyols (TERGITOL™ from DOW), biocides, such as isothiazolinones (ACTICIDE® from Thor), anticorrosives, such as benzotriazole, lubricants, dispersants, coalescing agents, crosslinking agents, wetting agents, plasticizers, antioxidants, UV stabilizers.

Another subject-matter of the disclosure relates to writing instruments comprising:

an axial barrel containing a thermochromic ink composition according to the disclosure, and a pen body which delivers the thermochromic ink composition stored in the axial barrel.

These instruments generally consist of a body comprising the ink composition of the disclosure, and possibly a friction member.

The writing instrument of the disclosure is more specifically chosen from ballpoint pens, brush pens, colored pencils, highlighters, chalks and felt pens, and even more specifically ballpoint pens erasable by friction. In a preferred embodiment, the writing instrument is a ballpoint pen erasable by friction, more specifically with a flow rate of between 10 and 700 mg/200 m of writing, and even more specifically between 250 and 650 mg/200 m of writing.

The friction member of the writing instrument is more specifically a rubber.

The supports on which the ink composition of the disclosure can be applied are paper, fibers, leather, plastic, glass, metal, wood, concrete.

In addition to the foregoing, the disclosure also comprises other provisions which will emerge from the additional description which follows, which relates to the use of diester of bisphenol fluorene compounds of formula (I) according to the disclosure as a temperature change control agent in thermochromic pigment compositions, and their characterization.

EXAMPLES

Preparation of a diester of bisphenol fluorene compound (1) of formula (I):

Compound (1)

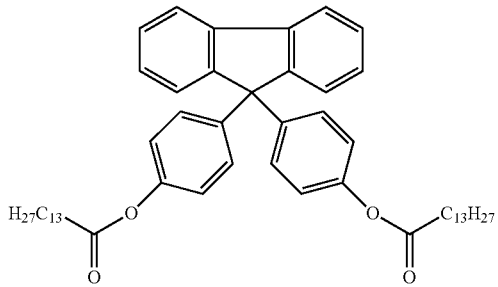

The compound (1) was synthesized according to two distinct methods:
Method 1: Esterification Via Acid Chloride In this method, 14.2 g of bisphenol FL (CAS number: 3236-71-3) was solubilized in 300 mL of tetrahydrofuran (THF, CAS number: 109-99-9). 4.0 g of triethylamine (CAS number: 121-44-8), used as a catalyst, was then added. The reaction mixture was then cooled and maintained at a temperature of 0° C. The temperature of the reaction mixture was maintained by a cold bath comprising dry-ice in ethanol. The reaction mixture was rendered inert by the incorporation of nitrogen gas into the reaction vessel. To the reaction vessel was slowly added 20.0 g of myristoyl chloride (CAS number: 112-64-1), drop-by-drop, over the period of 30 minutes. The bisphenol/acid chloride molar ratio used was ½. After complete addition of the acid chloride, the reaction vessel was heated to 25° C., and stirred under mechanical agitation for 2 hours.

The crude reaction mixture was extracted with 200 mL of ethyl acetate. The recovered organic phase was washed three times with 200 mL of distilled water. The organic phase was then dried with magnesium sulphate, filtered, and the solvent removed by rotary evaporation. The recovered residue was then recrystallized twice from ethanol, yielding compound (1) at a purity of >98%, as confirmed by gas chromatography (GC).

Method 2: Esterification Via Carboxylic Acid

In this method, 19.2 g of bisphenol FL (CAS number: 3236-71-3) was condensed with 50.0 g of myristic acid (CAS number: 544-63-8), the carboxylic acid compound serving as solvent. The carboxylic acid compound was used in excess, at a molar ratio of 4/1. 1.9 g of para-toluenesulfonic acid (pTs-OH, CAS number: 104-15-4), an organo-soluble acidic catalyst, was added at a catalyst/bisphenol molar ratio of 0.05/1. The reaction mixture was then heated to a temperature of 160° C., under a reduced pressure of 400 mbars, during 1 day. The reaction was terminated when the bisphenol was completely consumed, as verified by thin layer chromatography. The compound (1) obtained was recovered from the reaction mixture and purified by repeated recrystallizations from ethanol, yielding compound (1) at a purity of >97%, as confirmed by gas chromatography (GC).

Preparation of a Thermochromic Pigment Composition

A thermochromic pigment composition was prepared by mixing 2.2 parts by weight of 3-(4-diethylamino-2-ethoxyphenyl)-3-(1-ethyl-2-methylindol-3-yl)-4-azaphthalide (compound (A), Blue 63, CAS number: 69898-40-4), 2.5 parts by weight of 4,4'-(hexafluoroisopropylidene)diphenol (Compound (B1), bisphenol AF, CAS number: 1478-61-1), 2.5 parts by weight of 2,2-bis(4-hydroxy-3-methylphenyl)propane (compound (B2), CAS number: 79-97-0), and 92.8 parts by weight of compound (1) previously prepared by method 1 (compound (C)).

The mixture obtained was heated, with stirring, at a temperature of 110° C. for 1 hour, until complete solubilization of the compounds (A), (B1) and (B2) in the compound (C).

Preparation of Thermochromic Pigment Microcapsules 7.8 parts by weight of an aqueous solution of a (maleic anhydride)-co-(maleic methylvinyl ether) copolymer (solution at 31% by weight of copolymer) was neutralized with 14.8 parts by weight of an aqueous solution of sodium hydroxide (solution at 1.0 M) to pH=4.5. The resulting solution was diluted with 31.4 parts by weight of water, and the mixture was homogenized with a homogenizing mixer at a speed of 15 m·s$^{-1}$, during 1 hour. 27.4 parts by weight of the previously prepared thermochromic pigment composition was added and the emulsion formed was maintained at a temperature of 85° C. for a period of 30 minutes. 18.6 parts by weight of a melamine-formaldehyde prepolymer solution (aqueous solution at 50% by weight of prepolymer) was slowly added to the mixture over 10 minutes. After complete addition of the prepolymer solution, the mixture was heated at a temperature of 90° C. for 4 hours, at a speed of 15 m·s$^{-1}$.

The thermochromic pigment microcapsules were recovered as a water-based dispersion, also known as a slurry.

The slurry consisted of thermochromic pigment microcapsules dispersed in an aqueous solvent, the microcapsules having a d90 diameter of 5.2 μm, determined using an Zetasizer Nano ZS system, Malvern Instruments, under illumination at 632 nm.

The obtained thermochromic pigment microcapsules have the property of changing color from blue to colorless above 68° C. with a hysteresis effect of the color-change.

Preparation of a Thermochromic Ink Composition 15 parts by weight of glycerol were heated to 30° C. under agitation with a mechanical stirrer. 0.25 parts by weight of benzotriazole, 0.25 parts by weight of an aqueous biocide solution (which contains 2.5% by weight of 1,2-benzoisothiazolin-3-one and 2.5% by weight of 2-methyl-4-isothiazolin-3-one), 0.5 parts by weight of an aqueous dispersion of a polysiloxane polymer (which contains 50% by weight of polymer), and 0.5 parts by weight of a polyether polyol were subsequently added to the mixture. The mixture was stirred at 30° C. during about 15 minutes, until complete dissolution of the benzotriazole. Once homogeneous, 0.5 parts by weight of xanthan gum were added and incorporated under mechanical stirring over 15 minutes. After dispersion of the xanthan gum, 33 parts by weight of demineralized water were added slowly over 15 minutes. The hydrated mixture was left to stir under mechanical agitation for 3 hours. To this mixture was added 49.5 parts by weight of the thermochromic microcapsules slurry composition prepared previously. pH was controlled to pH=8 by the addition of 0.5 parts by weight of triethanolamine. The obtained blue colored ink composition was then dispersed using a high-speed disperser at a tangential velocity of at least 15 ms$^{-1}$ for 30 minutes. The prepared ink composition was then degassed under reduced pressure (between 100 and 400 mbar) prior to injection into ink cartridges.

Determination of the discoloration and recoloration temperatures of the thermochromic pigment microcapsules comprising compound (1):

The transition temperatures of the thermochromic pigment microcapsules obtained were measured by differential scanning calorimetry (DSC) using a TA Instruments Q20 apparatus, on a temperature range from −50 to 100° C., at cooling/heating speeds of 20° C./minute. The temperatures measured are shown in Table 1 below.

TABLE 1

Transition temperatures of thermochromic pigment microcapsules according to the Example

| | Color-change colored ↔ colorless | T1 (° C.) | T2 (° C.) | T3 (° C.) | T4 (° C.) | $T_H$ (° C.) | $T_G$ (° C.) | Δ H |
|---|---|---|---|---|---|---|---|---|
| Thermochromic pigment compositions comprising compound (1) | blue ↔ colorless | −5 | 5 | 55 | 68 | 0 | 62 | 62 |

The transition temperatures are indicated below:
T1: Full recoloration temperature,
T2: Partial recoloration temperature,
T3: Partial discoloration temperature,
T4: Full discloration temperature, $$T_H = \frac{T1 + T2}{2},$$

$$T_G = \frac{T3 + T4}{2},$$

$$\Delta H = \text{hysteresis window} = T_G - T_H.$$

Comparative Examples

Comparative examples were carried out according to the same procedure of the Example of the disclosure but by replacing the diester of bisphenol fluorene compound (1) of the disclosure prepared by method 1 by the bisphenol FL (CAS number: 3236-71-3) of formula:

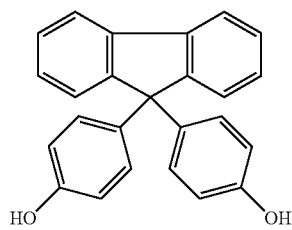 [SMILES: Oc1ccc(C2(c3ccc(O)cc3)c3ccccc3-c3ccccc32)cc1]

The composition of the thermochromic pigment compositions tested are presented in Table 2 below. The sole difference with the thermochromic pigment composition previously described in the absence of 2,2-bis(4-hydroxy-3-methylphenyl)propane (compound (B2)), and the variation of compounds (A), (B) and Compound (1) as follows:

TABLE 2

Compositions of the tested thermochromic pigment compositions

| Component | % by weight | Component | % by weight |
|---|---|---|---|
| Thermochromic pigment compositions according to the disclosure ||||
| Compound (A), Blue 63, CAS number: 69898-40-4 | 1 | Compound (A), Blue 63, CAS number: 69898-40-4 | 1 |
| Compound (B), bisphenol AF, CAS number: 1478-61-1 | 2 | Compound (B), bisphenol AF, CAS number: 1478-61-1 | 6 |
| Compound (1) | 97 | Compound (1) | 93 |

TABLE 2-continued

Compositions of the tested thermochromic pigment compositions

| Component | % by weight | Component | % by weight |
|---|---|---|---|
| Comparative thermochromic pigment compositions ||||
| Compound (A), Blue 63, CAS number: 69898-40-4 | 1 | Compound (A), Blue 63, CAS number: 69898-40-4 | 1 |
| Compound (B), bisphenol AF, CAS number: 1478-61-1 | 2 | Compound (B), bisphenol AF, CAS number: 1478-61-1 | 6 |
| Bisphenol FL (CAS number: 3236-71-3) | 97 | Bisphenol FL (CAS number: 3236-71-3) | 93 |

The compositions comprising the compound (1) of the disclosure as reaction medium demonstrated reversible thermochromic behavior, with color loss above 70° C. and recoloration occurring at temperatures below 30° C. (prior to encapsulation).

On the contrary, bisphenol-FL has a melting point of 225° C., which far exceeds the target melting range of 50-75° C. for thermochromic pigment compositions. The heating of both comparative compositions at 250° C. (above the melting point of bisphenol-FL) caused permanent decomposition and discoloration of the color-developing organic compound (leuco-dye). Therefore, no thermochromic effect was observed. Bisphenol FL is thus obviously unsuitable for use as a reaction medium in thermochromic pigment compositions.

The invention claimed is:
1. Method of regulating temperature change in a thermochromic ink composition, comprising incorporating into the composition a compound represented by the following formula (I):

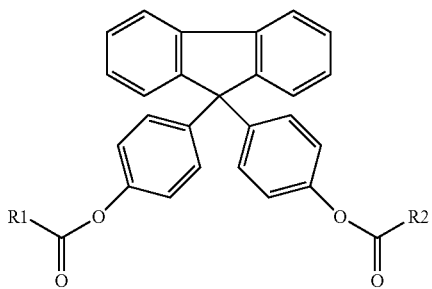

(I)

wherein R1 and R2, identical or different, represent a $C_2$-$C_{30}$ alkyl group, a $C_2$-$C_{30}$ alkenyl group, a $C_2$-$C_{30}$ alkynyl group, or a $C_2$-$C_{30}$ alkoxy group, wherein the groups are optionally substituted with at least one hydroxy, halogen, amino, $C_1$-$C_8$ alkyl, or $C_1$-$C_8$ alkoxy group.

2. The method according to claim 1, wherein R1 and R2 are identical and represent a linear or branched $C_2$-$C_{30}$ alkyl group.

3. The method according to claim 1 wherein R1 and R2 are identical and represent a linear or branched $C_6$-$C_{30}$ alkyl group.

4. A thermochromic pigment composition comprising:
(A) an electron-donating color-developing organic compound,
(B) an electron-accepting compound, and
(C) a compound represented by the formula (I) according to claim 1 as a reaction medium which controls color reaction between said components (A) and (B).

5. The thermochromic pigment composition according to claim 4, wherein the compound (A) is selected from the group consisting of
3-(4-diethylamino-2-ethoxyphenyl)-3-(1-ethyl-2-methyl-indol-3-yl)-4-azaphthalide (Blue 63, CAS number: 69898-40-4),
2'-(dibenzylamino)-6'-(diethylamino)fluoran (CAS number: 34372-72-0),
N,N-dimethyl-4[2-[2-(octyloxy)phenyl]-6-phenyl-4-pyridinyl]benzenamine (Yellow CK37, CAS number: 144190-25-0),
7-(4-diethylamino-2-hexyloxyphenyl)-7-(1-ethyl-2-methyl-1H-indol-3-yl)-7H-furo[3,4-b]pyridin-5-one (Blue 203, CAS number: 98660-18-5),
2-(2,4-dimethylphenylamino)-3-methyl-6-diethylamino-fluoran (Black 15, CAS number: 36431-22-8),
3,3-bis-(1-butyl-2-methyl-indol-3-yl)-3H-isobenzofuran-1-one (Red 40, CAS number: 50292-91-6),
and mixtures thereof.

6. The thermochromic pigment composition according to claim 4, wherein the compound (B) is selected from the group consisting of
2,2-bis(4-hydroxy-3-methylphenyl)propane (bisphenol C, CAS number: 79-97-0),
4-hexyl-1,3-dihydroxybenzene (4-hexylresorcinol, CAS number: 136-77-6),
4,4'-cyclohexylidenebisphenol (BPZ, CAS number: 843-55-0),
4,4'-(hexafluoroisopropylidene)diphenol (bisphenol AF, CAS number: 1478-61-1),
4,4'-(1-phenylethylidene)bisphenol (CAS number: 1571-75-1),
2,2'-dihydroxybiphenyl (CAS number: 1806-29-7),
4,4'-(1,4-phenylenediisopropylidene)bisphenol (CAS number: 2167-51-3),
1,1-bis(4-hydroxy-3-methylphenyl)cyclohexane (CAS number: 2362-14-3), 9,9-bis(4-hydroxyphenyl)fluorene (CAS number: 3236-71-3),
4,4'-(1,3-phenylenediisopropylidene)bisphenol (CAS number: 13595-25-0),
1,1,1-tris(4-hydroxyphenyl)ethane (CAS number: 27955-94-8),
4,4'-(2-ethylhexylidene)diphenol (CAS number: 74462-02-5),
α,α,α'-tris(4-hydroxyphenyl)-1-ethyl-4-isopropylbenzene (CAS number: 110726-28-8),
and mixtures thereof.

7. A thermochromic pigment microcapsule encapsulating a thermochromic pigment composition according to claim 4.

8. A thermochromic ink composition comprising thermochromic pigment microcapsules according to claim 7, and a carrier.

9. The thermochromic ink composition according to claim 8, wherein the thermochromic pigment microcapsules are present in an amount of 5 to 40% by weight relative to the total weight of the thermochromic ink composition.

10. A writing instrument comprising:
an axial barrel containing a thermochromic ink composition according to claim 8, and
a pen body which delivers the thermochromic ink composition stored in the axial barrel.

11. The writing instrument according to claim 10, further comprising a friction member.

12. A writing instrument according to claim 10, selected from the group consisting of ballpoint pens, brush pens, colored pencils, highlighters, chalks and felt pens.

13. The thermochromic pigment composition according to claim 4, wherein R1 and R2 are identical and represent a linear or branched $C_2$-$C_{30}$ alkyl group.

14. The thermochromic pigment composition according to claim 4, wherein R1 and R2 are identical and represent a linear or branched $C_4$-$C_{20}$ alkyl group.

15. The thermochromic pigment composition according to claim 4, wherein R1 and R2 are identical and represent a linear or branched $C_6$-$C_{30}$ alkyl group.

16. A writing instrument according to claim 15, wherein the writing instrument is ballpoint pens erasable by friction.

17. A compound represented by the following formula (II) according to claim 16, wherein R1a and R2b, identical or different, represent a linear or branched $C_6$-$C_{18}$ alkyl group.

18. A compound represented by the following formula (II) according to claim 16, wherein R1a and R2b, identical or different, represent a linear $C_{13}$ alkyl group.

19. The thermochromic pigment composition according to claim 4, wherein R1 and R2 are identical and represent a linear or branched $C_6$-$C_{18}$ alkyl group.

20. A compound represented by the following formula (II):

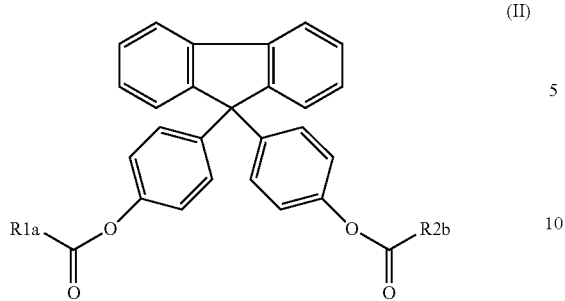
wherein R1a and R2b, identical or different, represent a linear or branched $C_6$-$C_{30}$ alkyl group.
* * * * *